United States Patent
Ritschl

(10) Patent No.: US 11,406,336 B2
(45) Date of Patent: Aug. 9, 2022

(54) TOMOSYNTHESIS METHOD WITH COMBINED SLICE IMAGE DATASETS

(71) Applicant: Siemens Healthcare GmbH, Erlangen (DE)

(72) Inventor: Ludwig Ritschl, Buttenheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 118 days.

(21) Appl. No.: 17/023,785

(22) Filed: Sep. 17, 2020

(65) Prior Publication Data
US 2021/0093271 A1 Apr. 1, 2021

(30) Foreign Application Priority Data
Sep. 27, 2019 (EP) .................................... 19200206

(51) Int. Cl.
*A61B 6/00* (2006.01)
*G06T 7/38* (2017.01)
*A61B 6/02* (2006.01)

(52) U.S. Cl.
CPC .............. *A61B 6/463* (2013.01); *A61B 6/025* (2013.01); *A61B 6/4021* (2013.01); *A61B 6/54* (2013.01); *G06T 7/38* (2017.01); *G06T 2207/10081* (2013.01)

(58) Field of Classification Search
CPC ....... A61B 6/463; A61B 6/025; A61B 6/4021; A61B 6/54; A61B 6/027; A61B 6/4078; A61B 6/466; A61B 6/469; A61B 6/5235; A61B 6/50; A61B 6/40; A61B 6/4208; A61B 6/502; A61B 6/52; G06T 7/38; G06T 2207/10081; G06T 7/33; G06T 7/593;
(Continued)

(56) References Cited

U.S. PATENT DOCUMENTS

| 2014/0254910 | A1 | 9/2014 | Jerebko et al. |
| 2016/0166329 | A1 | 6/2016 | Langan et al. |
| 2016/0334964 | A1 | 11/2016 | Jeon et al. |

(Continued)

OTHER PUBLICATIONS

Luckner Christph et al. "Parallel-Shift Tomosynthesis for Orthopedic Applications" Proc. SPIE 10573, Medical Imaging 2018: Physics of Medical Imaging, 105730G (Mar. 9, 2018); https://doi.org/10.1117/12.2292384.

(Continued)

*Primary Examiner* — Courtney D Thomas
(74) *Attorney, Agent, or Firm* — Harness, Dickey & Pierce, P.L.C.

(57) ABSTRACT

A method and image generating unit are for capturing at least two tomosynthesis images of an object undergoing examination offset by an angle of examination. In an embodiment the method includes a first and second capture of a plurality of first projection images along the linear trajectory, via X-ray source and the X-ray detector capturing the object undergoing examination in a first plane of capture and in a second capture plane different from the first capture plane, the first and second capture planes forming the angle of examination; determination of a first slice image dataset based upon the first projection images and of a second slice image dataset based upon the second projection images; and registration of the first slice image dataset and the second slice image dataset.

20 Claims, 5 Drawing Sheets

(58) Field of Classification Search
CPC . G06T 2207/10112; G06T 2207/10116; G06T 2207/30008
See application file for complete search history.

(56) References Cited

U.S. PATENT DOCUMENTS

2017/0132792 A1    5/2017  Jerebko et al.
2017/0367665 A1*  12/2017  Schlecht .............. A61B 6/5258

OTHER PUBLICATIONS

Extended European Search Report for European Application No. 19200206.1 dated Mar. 23, 2020.

* cited by examiner

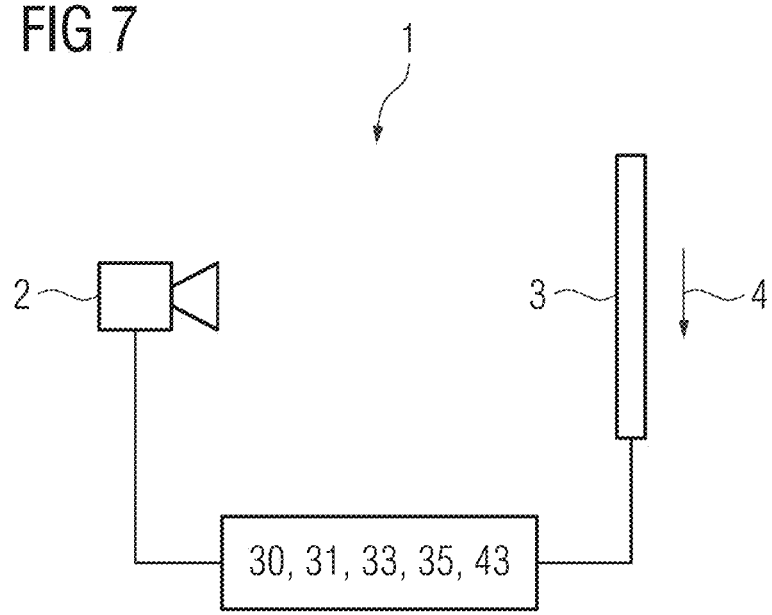

TOMOSYNTHESIS METHOD WITH COMBINED SLICE IMAGE DATASETS

PRIORITY STATEMENT

The present application hereby claims priority under 35 U.S.C. § 119 to European patent application number EP 19200206.1 filed Sep. 27, 2019, the entire contents of which are hereby incorporated herein by reference.

FIELD

Embodiments of the invention generally relate to a method for capturing at least two tomosynthesis images of an object undergoing examination that are offset by a predetermined angle of examination and can be combined into a common display.

BACKGROUND

Conventionally, tomosynthesis methods are used for breast imaging. In this case, the X-ray source can be arranged such that it can be displaced linearly, parallel to the compression device and the X-ray detector. As an alternative or in addition, the X-ray emitter can be arranged so that it is displaceable in a circle arc, in which case the circle arc is defined about an axis of rotation oriented perpendicular to the system axis of a mammography system. In this way, a three-dimensional X-ray imaging, in particular a tomosynthesis, can be performed using the mammography installation. In general in the case of tomosynthesis, a three-dimensional image can be generated from two-dimensional images that are detected from different angles of the X-ray source in relation to the X-ray detector. The two-dimensional and/or three-dimensional images may be part of a tomosynthesis (image) dataset.

Tomosynthesis methods are increasingly being considered for orthopedic applications as well. For example, a tomosynthesis method for orthopedic issues is known from the publication by C. Luckner et al., "Parallel-Shift Tomosynthesis for Orthopedic Applications", SPIE Medical Imaging, Houston, 2018.

SUMMARY

Typically, when for example coronal and sagittal sectional images of an object undergoing examination are displayed simultaneously, this is based on a complete three-dimensional reconstruction. The inventor has identified as a problem the fact that, for this purpose, on the one hand the possibility of capture using computed tomography and on the other a minimum dose for the capture using computed tomography are necessary. In particular in the case of orthopedic issues, it is preferred to capture the image with the joints under load—that is to say in a standing position. Capture using computed tomography of a standing patient is not possible in all clinics or practices.

At least one embodiment of the invention provides a method for capturing at least two tomosynthesis images of an object undergoing examination that are offset by a predetermined angle of examination; an image generating unit; a medical X-ray system; a computer program product; and a computer-readable medium, which make it possible to display simultaneously slice images that have been captured from different directions of view at a reduced dose.

Embodiments of the invention are directed to a method for capturing at least two tomosynthesis images of an object undergoing examination that are offset by a predetermined angle of examination; an image generating unit; a medical X-ray system; a computer program product; and a computer-readable medium.

At least one embodiment of the invention relates to a method for capturing at least two tomosynthesis images of an object undergoing examination that are offset by a predetermined angle of examination. The object undergoing examination is arranged between an X-ray source and an X-ray detector. The X-ray source and/or the X-ray detector are moved in opposing parallel planes, in particular parallel and opposite one another, along a linear trajectory. The method according to at least one embodiment of the invention comprises the first capture, the second capture, determination and (image) registration. In the step of the first capture, a plurality of first projection images are captured along the linear trajectory, wherein the X-ray source and the X-ray detector capture the object undergoing examination in a first plane of capture. In the step of the second capture, a plurality of second projection images are captured along the linear trajectory, wherein the X-ray source and the X-ray detector capture the object undergoing examination in a second capture plane that is different from the first, wherein the first capture plane and the second capture plane form the angle of examination. In the step of the second capture, the X-ray source and the X-ray detector may move along the linear trajectory in the same direction or in the opposite direction to that of the first capture. In the determination step, a first slice image dataset based upon the first projection images and of a second slice image dataset based upon the second projection images is determined. In the registration step, the first slice image dataset and the second slice image dataset undergo registration, in particular in relation to one another.

Furthermore, at least one embodiment of the invention relates to an image generating unit for capturing at least two tomosynthesis images of an object undergoing examination that are offset by a predetermined angle of examination according to the method according to at least one embodiment of the invention, having a receiving unit, a determining unit and a registering unit. The receiving unit is intended for the first capture of a plurality of first projection images along the linear trajectory, wherein the X-ray source and the X-ray detector capture the object undergoing examination in a first capture plane, and for the second capture of a plurality of second projection images along the linear trajectory, wherein the X-ray source and the X-ray detector capture the object undergoing examination in a second capture plane that is different from the first, wherein the first capture plane and the second capture plane form the angle of examination. The determining unit is intended for the determination of a first slice image dataset based upon the first projection images and a second slice image dataset based upon the second projection images. The registering unit is intended for the registration of the first slice image dataset and the second slice image dataset. The advantages of the method according to at least one embodiment of the invention can be carried over to the device.

Furthermore, at least one embodiment of the invention relates to a medical X-ray system having an image generating unit according to at least one embodiment of the invention, for the purpose of carrying out a method according to the invention. The medical X-ray system is preferably a radiography system. The advantages of the method according to at least one embodiment of the invention can be carried over to the medical X-ray system.

Furthermore, at least one embodiment of the invention relates to a computer program product having a computer program that can be loaded directly into a memory facility of a control facility of an X-ray system, having program sections in order to perform all the steps of the method according to at least one embodiment of the invention when the computer program is executed in the control facility of the X-ray system.

Furthermore, at least one embodiment of the invention relates to a computer-readable medium on which program sections that can be read and executed by a computer unit are stored in order to perform all the steps of the method according to at least one embodiment of the invention when the program sections are executed by the computing unit. The image generating unit or a processor may preferably comprise the computing unit.

At least one embodiment of the invention relates to a method for capturing at least two tomosynthesis images of an object undergoing examination, the at least two tomosynthesis images being offset by an angle of examination, the object undergoing examination being arranged between an X-ray source and an X-ray detector, and at least one of the X-ray source and the X-ray detector being moved in opposing parallel planes along a linear trajectory the method comprising:

capturing a plurality of first projection images along the linear trajectory, the X-ray source and the X-ray detector capturing the object undergoing examination in a first plane of capture;

capturing a plurality of second projection images along the linear trajectory, the X-ray source and the X-ray detector capturing the object undergoing examination in a second capture plane, different from the first capture plane, wherein the first capture plane and the second capture plane form the angle of examination;

determining a first slice image dataset based upon the plurality of first projection images and determining a second slice image dataset based upon the plurality of second projection images; and registering the first slice image dataset and the second slice image dataset.

At least one embodiment of the invention relates to an image generating unit for capturing at least two tomosynthesis images of an object undergoing examination, offset by an angle of examination, the image generating unit comprising:

a receiving unit
to receive a plurality of first projection images captured along a linear trajectory, an X-ray source and an X-ray detector being configured to capture the object undergoing examination in a first capture plane, and
to receive a plurality of second projection images captured along the linear trajectory, the X-ray source and the X-ray detector being configured capture the object undergoing examination in a second capture plane, different from the first capture plane, the first capture plane and the second capture plane forming the angle of examination;

a determining unit to determine a first slice image dataset based upon the first projection images and to determine a second slice image dataset based upon the second projection images; and a registering unit to register the first slice image dataset and the second slice image dataset.

At least one embodiment of the invention relates to a medical X-ray system comprising the image generating unit of an embodiment.

At least one embodiment of the invention relates to a non-transitory computer program product storing a computer program, directly loadable into a memory facility of a control facility of an X-ray system, including program sections to enable performance of the method of an embodiment when the computer program is executed in the control facility of the X-ray system.

At least one embodiment of the invention relates to a non-transitory computer-readable medium storing program sections, readable and executable by a computer unit, to enable performance of the method of an embodiment when the program sections are executed by the computing unit.

At least one embodiment of the invention relates to a method for capturing at least two tomosynthesis images of an object undergoing examination, the at least two tomosynthesis images being offset by an angle of examination, the object undergoing examination being arranged between an X-ray source and an X-ray detector, and at least one of the X-ray source and the X-ray detector being moved in opposing parallel planes along a linear trajectory the method comprising:

receiving a plurality of first projection images captured along a linear trajectory, an X-ray source and an X-ray detector being configured to capture the object undergoing examination in a first capture plane to create the plurality of first projection images;

receiving a plurality of second projection images captured along the linear trajectory, the X-ray source and the X-ray detector being configured capture the object undergoing examination in a second capture plane to create the plurality of second projection images, the second capture plane being different from the first capture plane and the first capture plane and the second capture plane forming the angle of examination;

determining a first slice image dataset based upon the plurality of first projection images and determining a second slice image dataset based upon the plurality of second projection images; and registering the first slice image dataset and the second slice image dataset.

BRIEF DESCRIPTION OF THE DRAWINGS

Example embodiments of the invention will be explained in more detail below with reference to drawings, in which:

FIG. 7 shows a schematic representation of the X-ray system according to the invention, in a second form of embodiment.

DETAILED DESCRIPTION OF THE EXAMPLE EMBODIMENTS

Figure 1:
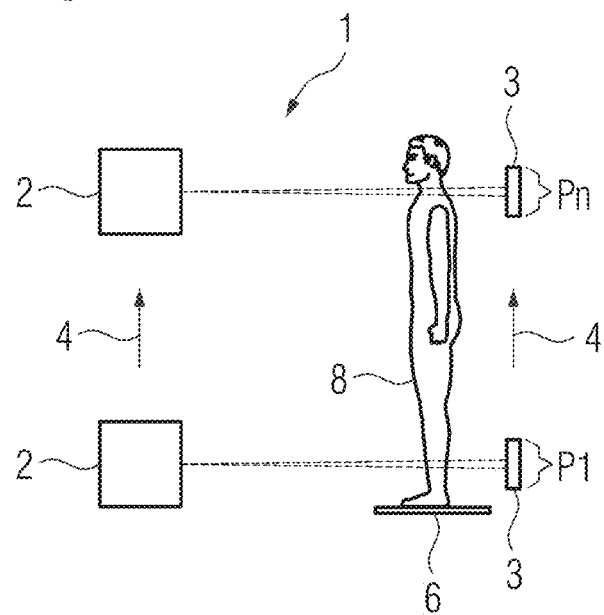
FIG. 1 shows a schematic representation of the X-ray system according to the invention, in a first form of embodiment, during capture in the first capture plane.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for capturing at least two tomosynthesis images of an object undergoing examination that are offset by a predetermined angle of examination. The object undergoing examination is arranged between an X-ray source and an X-ray detector. The X-ray source and/or the X-ray detector are moved in opposing parallel planes, in particular parallel and opposite one another, along a linear trajectory. The method according to at least one embodiment of the invention comprises the first capture, the second capture, determination and (image) registration. In the step of the first capture, a plurality of first projection images are captured along the linear trajectory, wherein the X-ray source and the X-ray detector capture the object undergoing examination in a first plane of capture. In the step of the second capture, a plurality of second projection images are captured along the linear trajectory, wherein the X-ray source and the X-ray detector capture the object undergoing examination in a second capture plane that is different from the first, wherein the first capture plane and the second capture plane form the angle of examination. In the step of the second capture, the X-ray source and the X-ray detector may move along the linear trajectory in the same direction or in the opposite direction to that of the first capture. In the determination step, a first slice image dataset based upon the first projection images and of a second slice image dataset based upon the second projection images is determined. In the registration step, the first slice image dataset and the second slice image dataset undergo registration, in particular in relation to one another.

The inventor has recognized that, instead of a complete three-dimensional reconstruction or capture using computed tomography, two tomosynthesis images that are offset, for example by 90 degrees, can be generated that enable sectional or slice image datasets that are each at an angle of examination to one another, for example at a right angle. Advantageously, the examination can be carried out at a significantly reduced dose. Advantageously, capture can be performed within a short period of time. Advantageously, by comparison with a capture using computed tomography, better accuracy can be achieved for high spatial frequencies.

The longitudinal axis of the body of the object undergoing examination, or a longitudinal axis of the region of the object undergoing examination that is being examined—for example an extremity—may be oriented in particular substantially parallel to the linear trajectory. The linear trajectory may for example extend along the longitudinal axis of the body, through the center point of the body.

The X-ray detector and/or the X-ray source move along the linear trajectory within a plane, this being spanned by a plane of capture. The term "along the linear trajectory" may mean that both the X-ray detector and the X-ray source move along the linear trajectory in the same direction, or that at least the X-ray source or the X-ray detector moves in the direction of the linear trajectory, or that the X-ray detector and the X-ray source move in opposing directions along or parallel to the linear trajectory. All the measured values of the X-ray detector that are read off during the first capture are measured in the first capture plane. All the measured values of the X-ray detector that are read off during the second capture are measured in the second capture plane.

The values measured by the X-ray detector, which form the projection dataset, can be used in a reconstruction step to generate a tomosynthesis dataset, wherein the depth information of the object undergoing examination is determined in each case along X-rays of the X-ray bundle from the X-ray source, such that different depth planes in the object have a different scan, parallel to the detection surface of the X-ray detector. If the X-ray detector and the X-ray source move simultaneously and parallel to one another in the same direction along the linear trajectory, the X-ray bundle in particular can be spanned by the movement along the linear trajectory and the X-ray beam fan of the X-ray source perpendicular to the linear trajectory—that is to say that the X-ray bundle may assume a chevron shape. For other types of movement of the X-ray source and the X-ray detector along the linear trajectory, for example with the X-ray source stationary or with movement in opposing directions, a substantially conical X-ray bundle can be formed. Reconstruction of the tomosynthesis dataset may be performed by a back-projection or maximum-likelihood method. The reconstruction enables a sectional or slice image or depth information to be determined. In particular, the tomosynthesis dataset may be at least partly a volume dataset.

In a determination step, a slice image having a slice thickness in a depth plane substantially parallel to the detection surface of the X-ray detector can be determined. The slice image is determined in the x-z direction or a-z direction. The slice image may be determined in particular using forward projection based upon the tomosynthesis dataset. The slice thickness may be determined along the y direction. The slice image, and in particular the slice center, is assigned to a y value.

In the registration step, the first slice image dataset and the second slice image dataset undergo registration in relation to one another. Registration may also be called image registration. The first slice image dataset and the second slice image dataset may be based on known methods of image registration adapted to the geometry in respect of the x-z direction or α-z direction. For this purpose, position data can be utilized during the capture—for example the position of the X-ray source and/or the X-ray detector. The slice images can be represented using the Cartesian coordinate system (x,y,z). As an alternative, the slice images can be represented using a specific coordinate system (α,y,z) taking into account the path angle α.

According to one embodiment of the invention, when the first slice image dataset and the second slice image dataset are determined, the depth information is determined in each case along a path having a path angle in relation to a Cartesian direction in space.

The different depth planes in the object, parallel to the detection surface, have a different scan. Here, a depth plane arranged closer to the X-ray source has a higher spatial scanning than a different depth plane arranged further away from the X-ray source. Thus, the spatial scanning in the x direction or the x-y plane depends on the y position of the depth plane, or a data point in the tomosynthesis dataset.

According to one embodiment of the invention, in the registration step the path angle is taken into account in each case in the first slice image dataset and the second slice image dataset. The path angle is $\alpha=\sin(x/SID)$, where the x direction is the Cartesian direction in space, and SID is the spacing between the X-ray source and the X-ray detector in the y direction. Advantageously, better depth information can be determined than with simple projectional radiographic imaging of the object. Advantageously, this angle-dependent depth information can be used when calculating slice images in order—in particular in the case of increasing path angles—to enable the calculating of particularly thick slice images to be more correct.

According to one embodiment of the invention, the angle of examination depends on the examination. The first and second capture planes may be selected in dependence on the examination, the region of examination or the type of examination. Advantageously, specifically the capture planes that are needed for diagnosis can be captured.

According to one embodiment of the invention, the angle of examination is substantially 90 degrees. For example, a coronal and a sagittal plane of capture can be selected.

According to one embodiment of the invention, a spacing between anatomical features or landmarks is determined based upon the first slice image dataset and the second slice image dataset. In particular three-dimensional measurements of bone positions can be performed. For this purpose, anatomical features or landmarks can be marked in the first and second slice image datasets. Marking may be performed automatically by way of an automatic identification, for example based upon segmenting or image recognition. As an alternative or in addition, marking may be performed by a user. The spacing between the anatomical features or landmarks, wherein at least one is marked in the first slice image dataset and at least one other is marked in the second slice image dataset, can be determined, in each case taking the path angle in the first slice image dataset and in the second slice image dataset into account. Advantageously, it is possible for measurement of bone positions to be improved based upon images using a radiography system. Advantageously, the patient dose can be reduced, since for the measurement it is possible to utilize images from the radiography system instead of captures using computed tomography. The term "three-dimensional measurement" in particular way that the anatomical features or landmarks do not appear within a single slice image and are only marked there. The anatomical features or landmarks may in particular be distributed over a plurality of slice images in the first and/or second slice image dataset and be marked in the respective slice image. A combined selection of two landmarks in the first slice image dataset and the second slice image dataset allows substantially exact 3D points in the object to be determined. This advantageously enables three-dimensional measurements of bone positions, and the planning of implants, within a three-dimensional representation.

According to one embodiment of the invention, the first slice image dataset and the second slice image dataset are displayed together. The first slice image dataset and the second slice image dataset may in particular be displayed simultaneously. The first slice image dataset and the second slice image dataset may in particular be displayed next to one another. Advantageously, during diagnosis information from different capture planes or perspectives can be utilized.

According to one embodiment of the invention, by way of a user input there is displayed in a first slice image of the first slice image dataset a corresponding second slice image in the second slice image dataset. By way of an input, for example by clicking on a position in a slice image of the first or second slice image dataset, the user can affect the display of the other slice image dataset, with the result for example that the position in both slice image datasets is displayed in the slice image respectively containing the position. When the position in the other slice image dataset is determined, in each case the path angle in the first slice image dataset and the second slice image dataset is taken into account. Advantageously, better transformation of a position from one slice image dataset to the other slice image dataset can be performed.

According to one embodiment of the invention, the user input moves a slide control in a first slice image of the first slice image dataset, with the result that the second slice image of the second slice image dataset, corresponding to the depth of the currently displayed slide control, is displayed. By actuating or displacing the slide control in a first slice image of the first slice image dataset, the second slice image of the second slice image dataset that is to be correspondingly displayed can be selected. This allows display of the first and second slice image datasets to be synchronized.

If for example a vertical bar is displayed in the first slice image at an x or α value, then there is displayed as the second slice image the slice image in which the depth or y value of the second slice image substantially corresponds to the x or α value in the first slice image. The first slice image, for example a border along the outer edges of the first slice image, and the slide control in the second slice image may have identical color coding. The depth or y value of the first slice image may correspondingly be superimposed on or displayed in the second slice image by way of a slide control at a corresponding x or α value. The second slice image, for example a border along the outer edges of the second slice image, and the slide control in the first slice image may have identical color coding, wherein the color of the coding of the first slice image and the slide control in the second slice image are different. For example, two different base colors or complementary colors may be used.

The slide control may be superimposed for example in the form of a bar along the x or z axis, or α or z axis, in a slice image in the first or second slice image dataset. The slide control may be superimposed as a horizontal or vertical bar in a slice image of the first or second slice image dataset.

The second slice image dataset may be scrolled through by moving the slide control or bar that is displayed superimposed or overlaid on the first slice image dataset. The converse is also true—that is to say that the first slice image dataset may be scrolled through by moving the slide control or bar that is displayed superimposed or overlaid on the second slice image dataset.

According to one embodiment of the invention, the course taken by an extended anatomical structure in a first slice image of the first slice image dataset is marked, and an assembled slice image based on the marked course and on the second slice image dataset is determined. The assembled slice image may be regarded as a second slice image. The assembled slice image may displayed for example as a second slice image or in addition to the second slice image. The marking may for example be made by the user, using the cursor. The marking may be made by segmenting or automatic image recognition. As a result of selecting or marking an in particular curved line in a first slice image of the first slice image dataset, it is possible to generate a so-called curved MPR—that is to say a curved multiplanar reformation—based upon the second slice image dataset.

As an alternative, as a result of selecting or marking an in particular curved line in a second slice image of the second slice image dataset, it is possible to generate a so-called curved MPR based upon the first slice image dataset. For example, a full sectional or slice image display of the spinal column may be displayed in an anterior-posterior view in an assembled slice image. Advantageously, an anatomical structure extending over a plurality of slice images in a capture plane can be displayed in an assembled slice image. Advantageously, this can enable diagnosis based on substantially corresponding views of a capture using computed tomography. Advantageously, the patient dose can be reduced.

Furthermore, at least one embodiment of the invention relates to an image generating unit for capturing at least two tomosynthesis images of an object undergoing examination that are offset by a predetermined angle of examination according to the method according to at least one embodiment of the invention, having a receiving unit, a determining unit and a registering unit. The receiving unit is intended for the first capture of a plurality of first projection images along the linear trajectory, wherein the X-ray source and the X-ray detector capture the object undergoing examination in a first capture plane, and for the second capture of a plurality of second projection images along the linear trajectory, wherein the X-ray source and the X-ray detector capture the object undergoing examination in a second capture plane that is different from the first, wherein the first capture plane and the second capture plane form the angle of examination. The determining unit is intended for the determination of a first slice image dataset based upon the first projection images and a second slice image dataset based upon the second projection images. The registering unit is intended for the registration of the first slice image dataset and the second slice image dataset. The advantages of the method according to at least one embodiment of the invention can be carried over to the device.

Furthermore, a reconstruction unit for reconstructing a tomosynthesis dataset can be provided, wherein the depth information of the object undergoing examination is determined in each case along X-rays of the X-ray bundle from the X-ray source, such that different depth planes in the object have a different scan, parallel to the detection surface. The image generating unit may further comprise a representation unit for representation or display. The computing unit may comprise at least some of the units. The representation unit may in particular take the form of a display unit, for example being formed as a screen.

Furthermore, at least one embodiment of the invention relates to a medical X-ray system having an image generating unit according to at least one embodiment of the invention, for the purpose of carrying out a method according to the invention. The medical X-ray system is preferably a radiography system. The advantages of the method according to at least one embodiment of the invention can be carried over to the medical X-ray system.

Furthermore, at least one embodiment of the invention relates to a computer program product having a computer program that can be loaded directly into a memory facility of a control facility of an X-ray system, having program sections in order to perform all the steps of the method according to at least one embodiment of the invention when the computer program is executed in the control facility of the X-ray system.

Furthermore, at least one embodiment of the invention relates to a computer-readable medium on which program sections that can be read and executed by a computer unit are stored in order to perform all the steps of the method according to at least one embodiment of the invention when the program sections are executed by the computing unit. The image generating unit or a processor may preferably comprise the computing unit.

FIG. 1 shows an example embodiment of the X-ray system 1 according to the invention, in a first form of embodiment, during capture in the first capture plane. The object undergoing examination 8 is arranged between an X-ray source 2 and an X-ray detector 3. The object undergoing examination 8 is standing on a base surface 6. The X-ray source 2 and the X-ray detector 3 are moved simultaneously in the same direction of movement, parallel and opposite one another along a linear trajectory 4.

The longitudinal axis of the body of the object undergoing examination 8 is oriented substantially parallel to the linear trajectory 4. The linear trajectory 4 may extend for example along the longitudinal axis of the body or parallel to the longitudinal axis of the body and through the center point of the body. The X-ray detector 3 moves along the linear trajectory 4 within a plane, this being spanned by a plane of capture.

Figure 2:
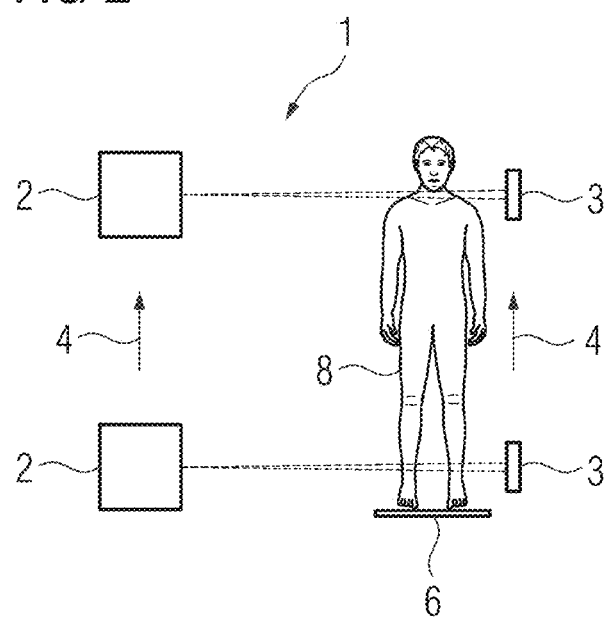
FIG. 2 shows a schematic representation of the X-ray system according to the invention, in a first form of embodiment, during capture in the second capture plane.

FIG. 2 shows an example embodiment of the X-ray system 1 according to the invention, in a first form of embodiment, during capture in the second capture plane. By comparison with FIG. 1, the patient is arranged turned through 90 degrees in relation to the first capture. The angle of examination is thus 90 degrees. Preferably, the X-ray system 1 has oriented itself with the object undergoing examination, displaced through 90 degrees in relation to the first capture. The X-ray detector 3 moves along the linear trajectory 4 within a plane, this being spanned by a second plane of capture. The second capture plane is thus oriented at a right angle in relation to the first capture plane.

As an alternative, the X-ray detector 3 and the X-ray source 2 may, for the purpose of capture in the first and the second capture planes, move in opposing directions along the linear trajectory 4 (not illustrated). As an alternative, for the purpose of capture in the first and the second capture planes, it is possible for only the X-ray source 2 to move along the linear trajectory 4, while the X-ray detector 3 remains stationary in a position (not illustrated).

Figure 3:
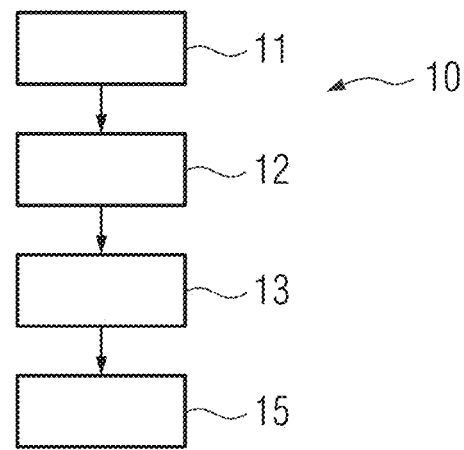
FIG. 3 shows a schematic representation of the method according to an embodiment of the invention.

FIG. 3 shows an example embodiment of the method 10 according to the invention. The method 10 serves for the capture of at least two tomosynthesis images of an object undergoing examination, which are offset by a predetermined angle of examination. The method 10 according to an embodiment of th invention has the steps of the first capture 11, the second capture 12, determining 13 and registering 15, preferably in this order. In the step of the first capture 11, a plurality of first projection images are captured along the linear trajectory, during which the X-ray source and the X-ray detector capture the object undergoing examination in a first capture plane. In the step of the second capture 12, a plurality of second projection images are captured along the linear trajectory, wherein the X-ray source and the X-ray detector capture the object undergoing examination in a second capture plane that is different from the first, wherein the first capture plane and the second capture plane form the angle of examination. In the step of the second capture 12, the X-ray source and the X-ray detector may move along the linear trajectory in the same direction or in the opposite direction to that of the first capture 11. In the step of determining 13, a first slice image dataset based upon the first projection images and from a second slice image dataset based upon the second projection images are determined. In the step of registering 15, the first slice image dataset and the second slice image dataset are registered.

Figure 4:
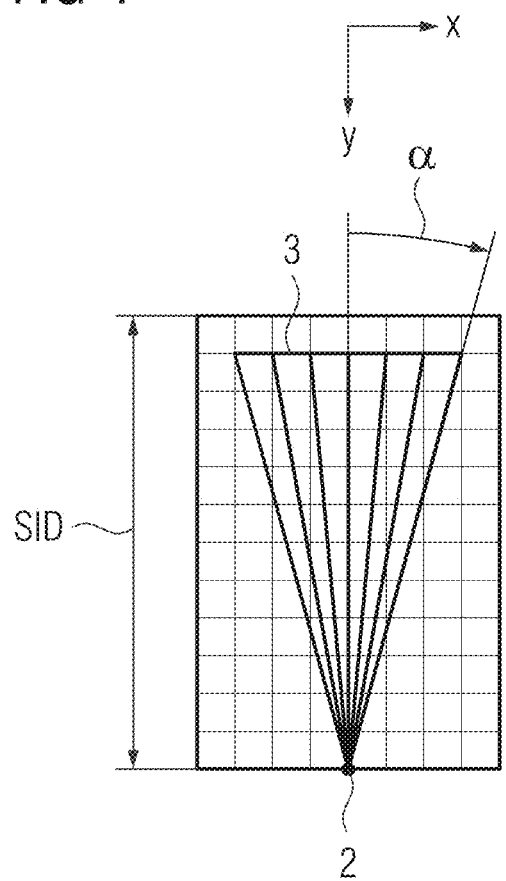
FIG. 4 shows a schematic representation of the first coordinate system in relation to the Cartesian coordinate system.

FIG. 4 shows an example embodiment of the first coordinate system in relation to the Cartesian coordinate system. The first coordinate system is the native coordinate system in the x-y plane, resulting from the capture geometry. The coordinates of a point between the X-ray source 2 and the X-ray detector 3 are now described by the coordinate transformation (x,y,z) to ($\alpha$,y,z) with $\alpha=\sin(x/SID)$, where SID is the spacing between the X-ray source 2 and the X-ray detector 3 in the y direction.

Figure 5:
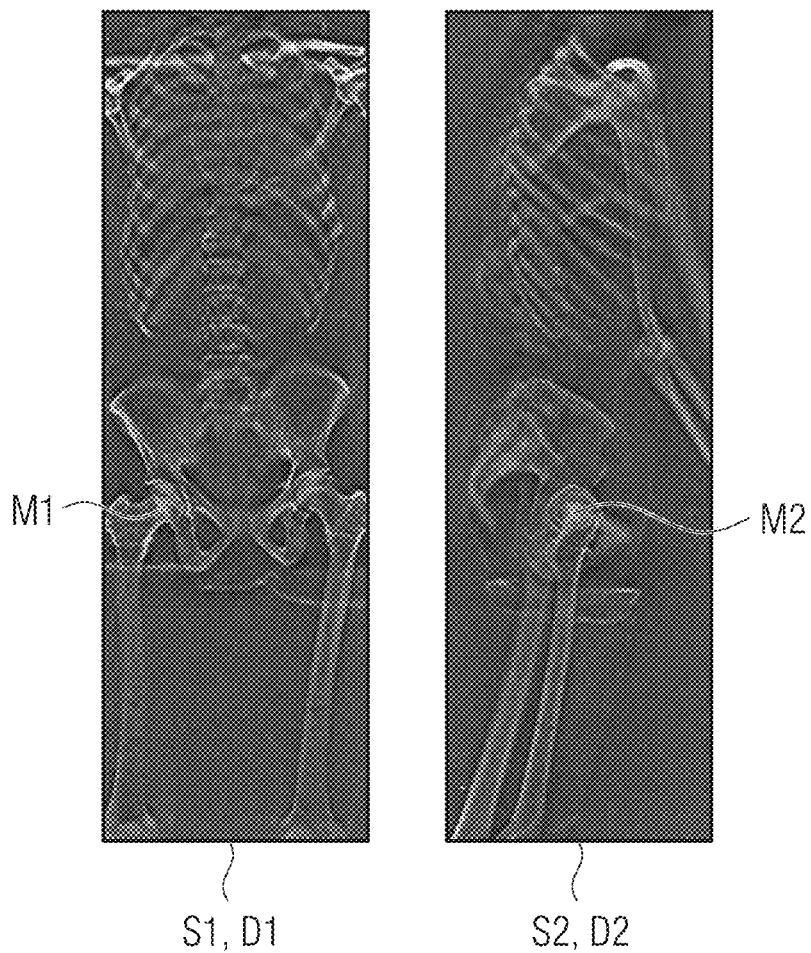
FIG. 5 shows a schematic representation of a display of determining spacing based upon the first slice image dataset and the second slice image dataset.

FIG. 5 shows a display of determining a spacing based upon the first slice image dataset and the second slice image dataset. Based upon the first slice image dataset D1 and the second slice image dataset D2, a spacing between anatomical features or landmarks is determined. In particular, three-dimensional measurements of bone positions are carried out. For this purpose, anatomical features or landmarks are marked in the first slice image dataset D1 and the second slice image dataset D2 by a mark M1, M2. The marking may be performed automatically by way of automatic identification, for example based upon segmentation or image recognition. As an alternative or in addition, the marking may be performed by a user. The spacing between the anatomical features or landmarks—with at least one being marked in the first slice image dataset D1 and at least one other being marked in the second slice image dataset D2—can be determined, in each case taking the path angle in the first slice image dataset D1 and in the second slice image dataset D2 into account. The anatomical features or landmarks are in particular distributed over the first slice image S1 of the first slice image dataset D1 and in the second slice image S2 of the second slice image dataset D2, and marked in the respective slice image by the mark M1 and M2 respectively.

Figure 6:
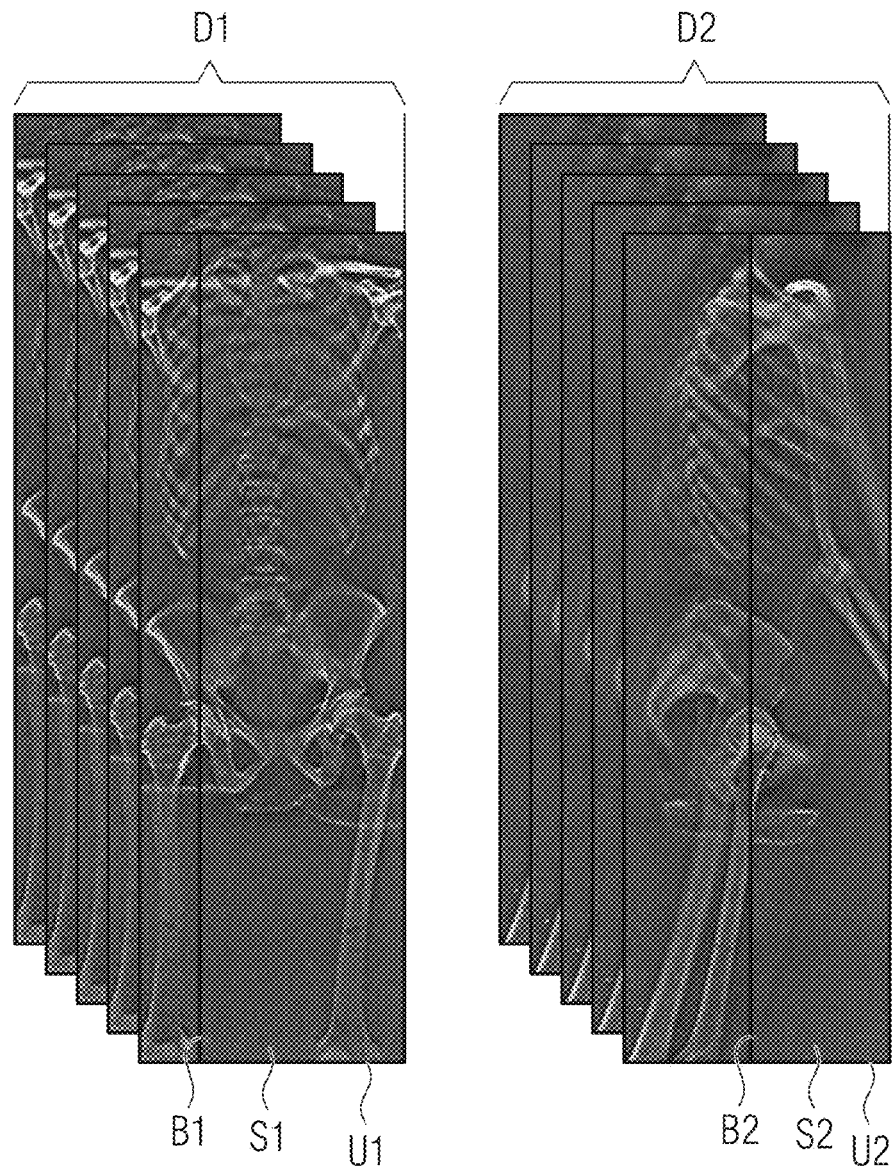
FIG. 6 shows a schematic representation of the display of the first slice image of the first slice image dataset and the corresponding second slice image of the second slice image dataset.

FIG. 6 shows an example embodiment of the inventive display of the first slice image S1 of the first slice image dataset D1 and the corresponding second slice image S2 of the second slice image dataset D2. By way of a user input, there is displayed in a first slice image S1 of the first slice image dataset D1 a corresponding second slice image S2 in the second slice image dataset D2. The user can, by way of an input—for example by clicking on a position in a slice image S1, S2 of the first slice image dataset D1 or second slice image dataset D2—affect the display of the other slice image dataset D1, D2 such that for example the position is displayed in both slice image datasets D1, D2 in the slice image S1, S2 respectively containing the position. When the position is determined in the other slice image dataset, in each case the path angle is taken into account in the first slice image dataset D1 and the second slice image dataset D2. A transformation of a position from one slice image dataset to the other slice image dataset is performed.

By way of the user input, a slide control B1 in a first slice image S1 of the first slice image dataset D2 is moved such that the second slice image S2 of the second slice image dataset D2, corresponding to the depth of the currently displayed slide control B1, is displayed. By actuating or displacing the slide control B1 in a first slice image S1 of the first slice image dataset D1, the second slice image S2 of the second slice image dataset D2 that is to be correspondingly displayed is selected. This synchronizes display of the first slice image dataset D1 and the second slice image dataset D2. If the vertical bar B1 in the first slice image S2 is displayed at an x or a value, then there is displayed as the second slice image S2 the slice image of the second slice image dataset D2, wherein the depth or y value of the second slice image S2 substantially corresponds to the x or $\alpha$ value in the first slice image S1. The first slice image S1 is marked in the form of a border U1 along the outer edges of the first slice image S1. The border U1 and the slide control B2 in the second slice image S2 have identical color coding. The depth or y value of the first slice image S1 may be correspondingly superimposed or displayed by way of a slide control B2 at a corresponding x or $\alpha$ value in the second slice image S2. The second slice image S2 has a border U2 along the outer edges of the second slice image S2. The border U2 and the slide control B1 in the first slice image S1 may have identical color coding, with the color of the coding of the first slice image S1 and the slide control B2 in the second slice image S2 being different. The slide control B1, B2 is superimposed in the form of a bar along the vertical z axis in a slice image of the first slice image dataset D1 or second slice image dataset D2.

The second slice image dataset D2 is scrolled through by moving the slide control B1 or bar that is displayed superimposed or overlaid on the first slice image dataset D1. The converse is also possible—that is to say that the first slice image dataset D1 can be scrolled through by moving the slide control B2 or bar that is displayed superimposed or overlaid on the second slice image dataset D2.

FIG. 7 shows an example embodiment of the X-ray system 1 according to the invention, in a second form of embodiment. The X-ray source 2 and the X-ray detector 3 are connected to one another by way of an image generating unit 30. The image generating unit may be a computing unit and/or control unit or control facility, or this may comprise it. The image generating unit 30 comprises the receiving unit 31, the determining unit 33 and the registering unit 35. Further, the image generating unit may have a display unit 43, for example taking the form of a screen.

Although the invention has been illustrated in detail by the preferred example embodiment, the invention is not restricted by the disclosed examples, and those skilled in the art will be able to derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a way-plus-function element within the meaning of 35 U.S.C. § 112(f) unless an element is expressly recited using the phrase "way for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for capturing at least two tomosynthesis images of an object undergoing examination, the at least two tomosynthesis images being offset by an angle of examination, the object undergoing examination being arranged between an X-ray source and an X-ray detector, and at least one of the X-ray source and the X-ray detector being moved in opposing parallel planes along a linear trajectory the method comprising:

capturing a plurality of first projection images along the linear trajectory, the X-ray source and the X-ray detector capturing the object undergoing examination in a first capture plane;

capturing a plurality of second projection images along the linear trajectory, the X-ray source and the X-ray detector capturing the object undergoing examination in a second capture plane, different from the first capture plane, wherein the first capture plane and the second capture plane form the angle of examination;

determining a first slice image dataset based upon the plurality of first projection images and determining a second slice image dataset based upon the plurality of second projection images; and registering the first slice image dataset and the second slice image dataset.

2. The method of claim 1, wherein, during respective determining of the first slice image dataset and the second slice image dataset, respective depth information is determined along a path having a path angle in relation to a Cartesian direction in space.

3. The method of claim 2, wherein during the respective registering of the first slice image dataset and the second slice image dataset, a respective path angle is taken into account in the respective first slice image dataset and the respective second slice image dataset.

4. The method of claim 2, wherein the angle of examination depends on the examination.

5. The method of claim 2, wherein the angle of examination is substantially 90 degrees.

6. The method of claim 2, further comprising:

determining a spacing between anatomical features or landmarks, based upon the first slice image dataset and the second slice image dataset.

7. The method of claim 1, wherein the angle of examination depends on the examination.

8. The method of claim 1, wherein the angle of examination is substantially 90 degrees.

9. The method of claim 1, further comprising:

determining a spacing between anatomical features or landmarks, based upon the first slice image dataset and the second slice image dataset.

10. The method of claim 1, further comprising:

displaying the first slice image dataset and the second slice image dataset, together.

11. The method of claim 10, wherein, during the displaying and via a user input, a first slice image of the first slice image dataset and a corresponding second slice image in the second slice image dataset, are displayed.

12. The method of claim 11, wherein the user input includes movement of a slide control in a first slice image of the first slice image dataset, resulting in the second slice image of the second slice image dataset, corresponding to a depth of the currently displayed slide control, being displayed.

13. The method of claim 1, further comprising:

marking a course taken by an extended anatomical structure in a first slice image of the first slice image dataset; and marking an assembled slice image, based on the course marked; and determining the second slice image dataset.

14. A non-transitory computer program product storing a computer program, directly loadable into a memory facility of a control facility of an X-ray system, including program sections to enable performance of the method of claim 1 when the computer program is executed in the control facility of the X-ray system.

15. A non-transitory computer-readable medium storing program sections, readable and executable by a computer unit, to enable performance of the method of claim 1 when the program sections are executed by the computing unit.

16. An image generating unit for capturing at least two tomosynthesis images of an object undergoing examination, offset by an angle of examination, the image generating unit comprising:
- a receiving unit
  - to receive a plurality of first projection images captured along a linear trajectory, an X-ray source and an X-ray detector being configured to capture the object undergoing examination in a first capture plane, and
  - to receive a plurality of second projection images captured along the linear trajectory, the X-ray source and the X-ray detector being configured capture the object undergoing examination in a second capture plane, different from the first capture plane, the first capture plane and the second capture plane forming the angle of examination;
- a determining unit to determine a first slice image dataset based upon the first projection images and to determine a second slice image dataset based upon the second projection images; and
- a registering unit to register the first slice image dataset and the second slice image dataset.

17. A medical X-ray system comprising the image generating unit of claim 16.

18. A method for capturing at least two tomosynthesis images of an object undergoing examination, the at least two tomosynthesis images being offset by an angle of examination, the object undergoing examination being arranged between an X-ray source and an X-ray detector, and at least one of the X-ray source and the X-ray detector being moved in opposing parallel planes along a linear trajectory the method comprising:
- receiving a plurality of first projection images captured along a linear trajectory, an X-ray source and an X-ray detector being configured to capture the object undergoing examination in a first capture plane to create the plurality of first projection images;
- receiving a plurality of second projection images captured along the linear trajectory, the X-ray source and the X-ray detector being configured to capture the object undergoing examination in a second capture plane to create the plurality of second projection images, the second capture plane being different from the first capture plane and the first capture plane and the second capture plane forming the angle of examination;
- determining a first slice image dataset based upon the plurality of first projection images and determining a second slice image dataset based upon the plurality of second projection images; and
- registering the first slice image dataset and the second slice image dataset.

19. The method of claim 18, wherein, during respective determining of the first slice image dataset and the second slice image dataset, respective depth information is determined along a path having a path angle in relation to a Cartesian direction in space.

20. The method of claim 19, wherein during the respective registering of the first slice image dataset and the second slice image dataset, a respective path angle is taken into account in the respective first slice image dataset and the respective second slice image dataset.

* * * * *